Figure 1:
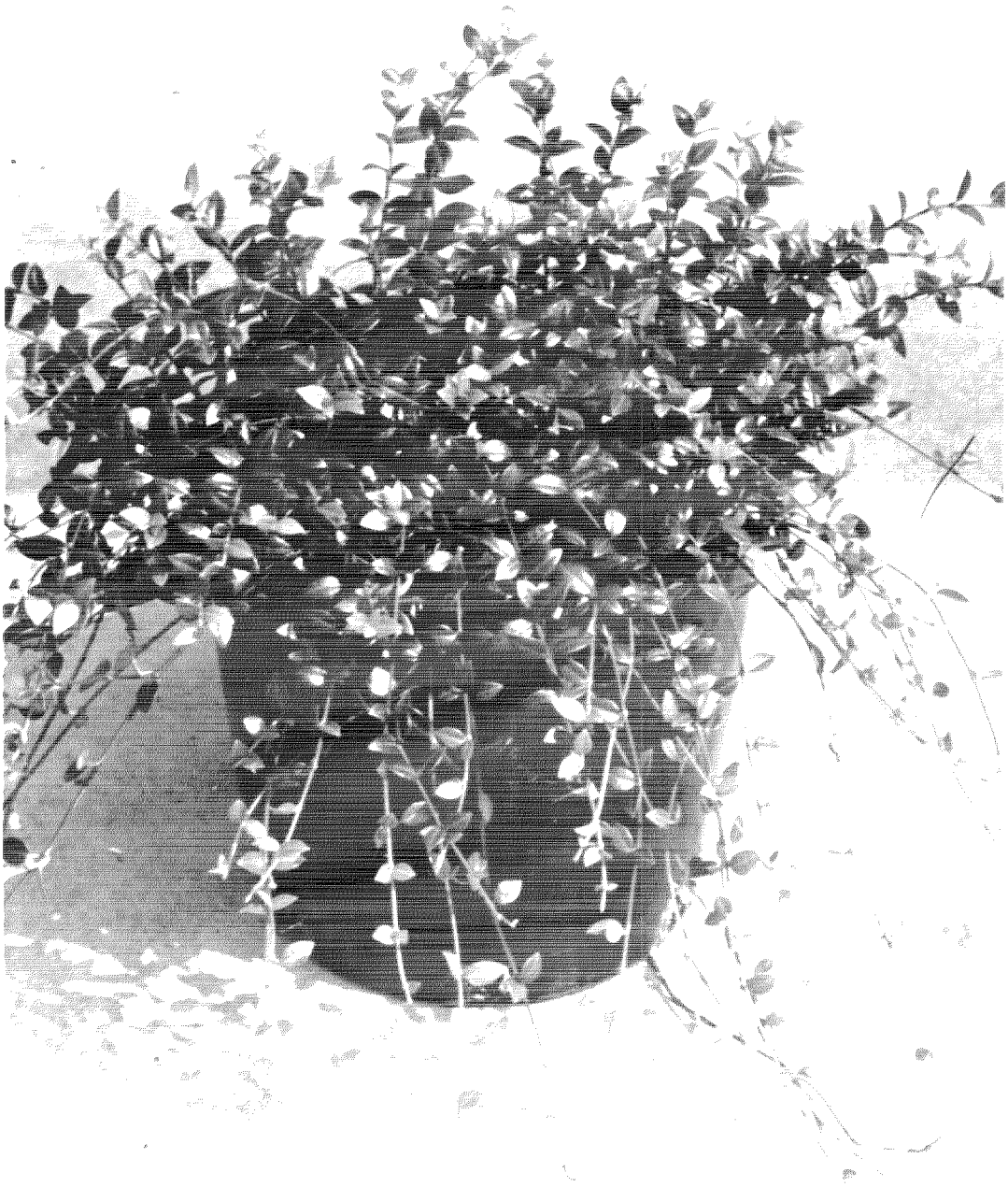

United States Patent [19]

Billeaud, III

[11] Patent Number: Plant 5,346

[45] Date of Patent: Nov. 20, 1984

[54] **DISTINCT CLONE OF THE SPECIES *TRACHELOSPERMUM ASIATICUM* CHARACTERIZED AS NOVEL BY ITS DWARF SIZE**

[76] Inventor: Hugh J. Billeaud, III, P.O. Box 284, New Iberia, La. 70560

[21] Appl. No.: 470,313

[22] Filed: Feb. 28, 1983

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Thomas E. Balhoff

[57] ABSTRACT

A new and distinct clone of the species *Trachelospermum asiaticum,* characterized as novel by its dwarf size.

1 Drawing Figure

1

The present invention relates to a new and distinct variety of plant (vine or ground cover) of the species *Trachelospermum asiaticum,* commonly known as Asian Jasmine, characterized as to novelty by its dwarf habit of growth. Overall size of the plant is less than the normal species. It exhibits smaller leaves and shorter internodes.

This new plant has mature leaves from 1½ to 2½ cm long, 1 to 1¼ cm wide with internodes from ½ to 2 cm long under full sun growing conditions.

The normal species has mature leaves from 2 to 4 cm long, 1½ to 2 cm wide with internodes from 1 to 8 cm long under full sun growing conditions.

These measurements and the color photographs give testimony to the reduced size of this new clone. The species is one of the most widely used vines for ground cover in the southeastern and gulf coast states. Its use, however, is limited by its aggressive vining habit. My new selection will reduce the amount of pruning required to maintain the plant.

The drawing illustrates the dwarf growth habit of my new plant.

This new and distinct clone was discovered and selected from a group of 250,000 cuttings under cultivation at my nursery at Jefferson Island, La. in 1979. The new plant was discovered as a mutation since plants of this species are propagated vegetatively by cuttings and in fact seldom bloom and have seldom been observed with seed pods. My new dwarf selection has never bloomed since its discovery. This factor is normal since the species tends to remain in the vegetative stage rather than lapse into the reproductive stage. The original plant has been maintained in cultivation with over 100,000 progeny at my nursery. To date no reversions

2 or mutations have been observed indicating the clone is stable.

The plant has survived a low temperature of 11° F. in January of 1980 exhibiting good winter hardiness.

Parentage: The parent plant which mutated into this new dwarf variety was the normal species widely cultivated in the South under the name Asian Jasmine. The new selection was discovered growing as a branch from the common type.

Growth: The plant is dwarf with smaller foliage and shorter internodes with a more prostrate growth habit as compared to the normal type.

Vines: Vines are produced freely and are self-branching. The vines are horizontal and light green maturing to brown. Vines eventually grow to 3 feet or more in length.

Foliage: Simple leaves with entire margins ovate in shape with an acute tip and an obtuse base on a stalked petiole are attached along the stem in an opposite arrangement. Leaf venation is pinnate. Leaves range in size from 1½–2½ cm long and 1–1¼ cm wide with internodes from 178 –2 cm under full sun growing conditions.

Flower: Blooming has not been observed since the discovery of this plant.

I claim:

1. A new and distinct variety of *Trachelosperum asiaticum* plant substantially as illustrated in FIG. I and described in the Specification, characterized by a dwarf growth habit.

* * * * *